United States Patent [19]
Klein et al.

[11] Patent Number: 5,889,011
[45] Date of Patent: Mar. 30, 1999

[54] SUBSTITUTED AMINO ALKYL COMPOUNDS

[75] Inventors: J. Peter Klein, Vashon Island; Gail E. Underiner; Alistair J. Leigh, both of Brier, all of Wash.

[73] Assignee: Cell Therapeutics, Inc., Seattle, Wash.

[21] Appl. No.: 884,037

[22] Filed: Jun. 27, 1997

Related U.S. Application Data

[63] Continuation of Ser. No. 149,681, Nov. 9, 1993, abandoned, which is a continuation-in-part of Ser. No. 973,804, Nov. 9, 1992, Pat. No. 5,340,813.

[51] Int. Cl.$^6$ .......................... C07D 473/00; A61K 31/52
[52] U.S. Cl. ..................... 514/263; 514/261; 544/267; 544/264; 544/265
[58] Field of Search ................... 544/257, 267, 544/263, 285, 287; 514/263, 261

[56] References Cited

U.S. PATENT DOCUMENTS

| | | | |
|---|---|---|---|
| 3,422,107 | 1/1969 | Mohler et al. | 544/271 |
| 3,737,433 | 6/1973 | Mohler et al. | 544/271 |
| 4,061,753 | 12/1977 | Bodor et al. | 424/253 |
| 4,275,064 | 6/1981 | Bodor et al. | 424/253 |
| 4,374,837 | 2/1983 | Favier et al. | 544/271 |
| 4,515,795 | 5/1985 | Hinze et al. | 544/267 |
| 4,558,051 | 12/1985 | Sunshine et al. | 514/261 |
| 4,565,817 | 1/1986 | Korbonits et al. | 544/267 |
| 4,576,947 | 3/1986 | Hinze et al. | 544/267 |
| 4,618,612 | 10/1986 | Baglioni et al. | 514/265 |
| 4,636,507 | 1/1987 | Kreutzer et al. | 514/263 |
| 4,784,994 | 11/1988 | Romer et al. | 514/183 |
| 4,833,146 | 5/1989 | Gebert et al. | 514/263 |
| 4,845,081 | 7/1989 | Sloan | 514/258 |
| 4,965,271 | 10/1990 | Mandell et al. | 514/263 |
| 5,039,666 | 8/1991 | Novick, Jr. | 514/39 |
| 5,096,906 | 3/1992 | Mandell et al. | 514/263 |
| 5,118,500 | 6/1992 | Hänel et al. | 424/85.1 |
| 5,126,340 | 6/1992 | Tseng et al. | 514/258 |
| 5,196,439 | 3/1993 | Sugimoto et al. | 514/318 |
| 5,247,086 | 9/1993 | Cain et al. | 544/281 |
| 5,272,153 | 12/1993 | Mandell et al. | 514/263 |
| 5,340,813 | 8/1994 | Klein et al. | 544/272 |
| B1 3,737,433 | 3/1987 | Mohler et al. | 544/268 |

FOREIGN PATENT DOCUMENTS 9205175  4/1992  WIPO.

OTHER PUBLICATIONS

Bianco et al., *Blood*, 76: Supplement 1 (522), p. 133a, "Pentoxifylline (PTX) and GM–CSF Decrease Transplantation (BMT)", 1991.

Bianco et al., *Blood*, vol. 78, No. 5, pp. 1205–1211, "Phase I–II Trial of Pentoxiflylline for the Prevention of Transplant–Related Toxicities Following Bone Marrow Transplantation", 1991.

Bursten et al., *The Journal of Biological Chemistry*, vol. 266, No. 31, pp. 20732–20743, "Interleukin–1 Rapidly Stimulates Lysophosphatidate Acyltransferase and Phosphatidate Phosphohydrolase activities in Human Mesangial Cells", Nov. 1991.

Davis et al., *Applied Environment Microbial.*, 48:2, pp. 327–331, "Microbial Models of Mammalian Metabolism: Microbial Reduction and Oxidation of Pentoxifylline", Aug. 1984.

Singer et al., *Bone Marrow Transplantation*, 10:19, pp. 19–25, "Effect of Methylxanthine Derivatives on T Cell Activation", 1992.

Adam et al. J. Amer. Chem. Soc., vol. 67 (1945) pp. 1271–1273.

*Primary Examiner*—Mukund J. Shah
*Assistant Examiner*—Pavanaram K Sripada
*Attorney, Agent, or Firm*—McDermott, Will & Emery

[57] ABSTRACT

Compounds and pharmaceutical compositions thereof comprise the formula:

$$(R)j\text{- (core moiety)},$$

including resolved enantiomers and/or diastereomers, hydrates, salts, solvates and mixtures thereof, wherein J is an integer from one to three, the core moiety is non-cyclic or comprises at least one, five- to seven-membered ring structure, R may be selected from the group consisting of hydrogen, halogen, hydroxyl, amino, substituted or unsubstituted benzyl, alkyl ($C_{1-6}$) or alkenyl ($C_{1-6}$), and at least one R has the formula I:

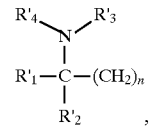

wherein n is an integer from four to eighteen; each $R'_1$ and $R'_2$ is independently hydrogen, alkyl ($C_{1-4}$) or alkenyl ($C_{1-4}$), the alkyl or alkenyl groups being preferably substituted by a halogen, hydroxyl, ketone or dimethylamino group and/or may be interrupted by an oxygen or hydrogen atom or an alkyl ($C_{1-4}$) group; and each $R'_3$ and $R'_4$ is independently hydrogen or methyl. Preferably, n is an integer from six to ten, $R'_1$ and $R'_2$ are independently hydrogen or methyl and $R'_3$ and $R'_4$ are hydrogen. The compounds are useful in treating or preventing, for example, sepsis syndrome, hematopoietic or organ toxicity, baldness, hair loss or alopecia caused by cytotoxic therapies, and progression of an inflammatory or autoimmune disease.

9 Claims, 9 Drawing Sheets

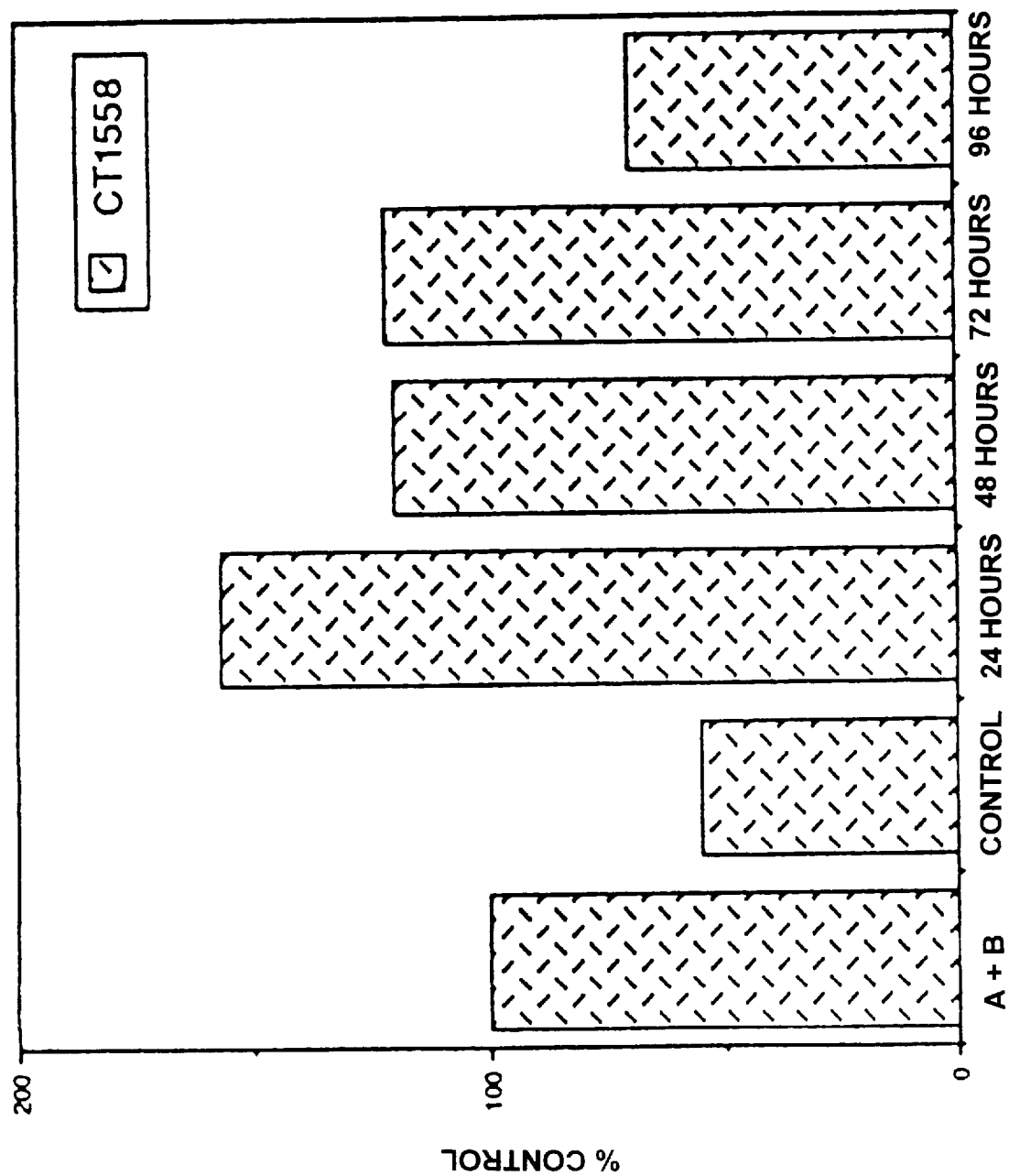

SUBSTITUTED AMINO ALKYL COMPOUNDS

CROSS REFERENCE TO RELATED APPLICATIONS

This is a continuation application of Ser. No. 08/149,681 filed Nov. 9, 1993, now abandoned which in turn is a continuation-in-part of application Ser. No. 07/973,804 filed Nov. 9, 1992 now U.S. Pat. No. 5,340,813.

TECHNICAL FIELD OF THE INVENTION

The invention provides a class of substituted amino alkyl compounds that are effective agents to inhibit specific cellular signaling events often induced by noxious or inflammatory stimuli, or to directly or indirectly (immune stimulation) be anti-microbial to yeast or fungal infections. More specifically, the inventive compounds have at least one amine-containing substituent bonded to core moiety. The inventive compounds are useful antagonists to control intracellular levels of specific non-arachidonyl sn-2 unsaturated phosphatidic acids and corresponding phosphatidic acid-derived diacylglycerols which occur in response to cellular proliferative stimuli.

BACKGROUND ART

Pentoxifylline (1-(5-oxohexyl)-3,7-dimethylxanthine), abbreviated PTX and disclosed in U.S. Pat. Nos. 3,422,107 and 3,737,433, is a xanthine derivative which has seen widespread medical use for the increase of blood flow. Metabolites of PTX were summarized in Davis et al., *Applied Environment Microbial.* 48:327, 1984. One such metabolite, 1-(5-hydroxyhexyl)-3,7-dimethylxanthine, designated M1 and disclosed in U.S. Pat. Nos. 4,515,795 and 4,576,947, increases cerebral blood flow. In addition, U.S. Pat. Nos. 4,833,146 and 5,039,666 disclose use of tertiary alcohol analogs of xanthine for enhancing cerebral blood flow.

U.S. Pat. No. 4,636,507 discloses that PTX and M1 stimulate chemotaxis in polymorphonuclear leukocytes in response to a chemotaxis stimulator. PTX and related tertiary alcohol substituted xanthines inhibit activity of certain cytokines to affect chemotaxis (U.S. Pat. No. 4,965,271 and U.S. Pat. No. 5,096,906). Administration of PTX and GM-CSF decrease tumor necrosis factor (TNF) levels in patients undergoing allogeneic bone marrow transplant (Bianco et al., *Blood* 76: Supplement 1 (522A), 1990). Reduction in bone marrow transplant-related complications accompanied reduction in assayable levels of TNF. However, in normal volunteers, TNF levels were higher among PTX recipients. Therefore, elevated levels of TNF are not the primary cause of such complications.

Therefore, effective therapeutic compounds that are safe and effective for human or animal administration and that can maintain cellular homeostasis in the face of a variety of inflammatory stimuli are needed. The invention is a result of research conducted in looking for such compounds.

SUMMARY OF THE INVENTION

We have found inventive compounds useful in a large variety of therapeutic indications for treating or preventing disease mediated by intracellular signaling through one or two specific intracellular signaling pathways. In addition, the inventive compounds and compositions are suitable for normal routes of therapeutic administration (e.g., parenteral, oral, topical, etc.) for providing effective dosages.

The invention provides a class of amine-derived compounds, preferably amine cyclic compounds. The inventive compounds and pharmaceutical compositions thereof have the formula:

(R)j- (core moiety), including resolved enantiomers and/or diastereomers, hydrates, salts, solvates and mixtures thereof, wherein j is an integer from one to three, the core moiety is either non-cyclic or comprises at least one five- to seven-membered ring structure, R may be selected from the group consisting of hydrogen, halogen (preferably bromine, chlorine, fluorine and iodine), hydroxyl, amino, substituted or unsubstituted benzyl, alkyl ($C_{1-6}$, preferably methyl) or alkenyl ($C_{1-6}$), preferably the alkyl or alkenyl groups being substituted by an hydroxy, halogen and dimethylamine and/or interrupted by an oxygen atom, wherein at least one R has the formula I:

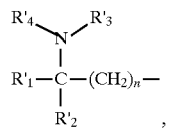

wherein n is an integer from four to eighteen; each $R'_1$ and $R'_2$ is independently hydrogen, alkyl ($C_{1-4}$) or alkenyl ($C_{1-4}$), the alkyl or alkenyl groups being preferably substituted by a halogen, hydroxyl, ketone or dimethylamino group and/or may be interrupted by an oxygen or hydrogen atom or an alkyl ($C_{1-4}$) group; and each $R'_3$ and $R'_4$ is independently hydrogen or methyl. Preferably, n is an integer from four to twelve (more preferably six to ten), $R'_1$ and $R'_2$ are independently hydrogen or methyl and $R'_3$ and $R'_4$ are hydrogen.

A non-cyclic core moiety may be, for example, an amino acid (one or two), an hydroxyl, carboxyl, sulfoxide, sulfonate, phosphate, amide, amine, or ketone group, a simple ionic functional group, or a terminal hydrogen or halogen atom. Exemplary core moiety amino acids may include one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be a dipeptide comprising two amino acids selected from the foregoing exemplary list. Exemplary core halogen atoms include bromine, chlorine, fluorine and iodine.

A core moiety may alternatively be at least one five- to seven-membered ring, preferably having from one to three, five- to six-membered ring structures in a predominantly planar configuration. Preferably, amino alkyl substituent R is bonded to a ring nitrogen if one exists. Exemplary, ring-core moieties may be substituted or unsubstituted: barbituric acid; benzamide; benzene; biphenyl; cyclohexane, cyclohexene; cyclohexanedione; cyclopentanedione; delta-lactam; flutarimide; glutarimide; homophthalimide; imidazole amide; isocarbostyrile; lumazine; napthlalene; pteridine; pthalimide; piperidine; pyridine; pyrimidine; pyrrole amide; quinazolinedione; quinazolinone; quinolone; recorsinol; stilbene; succinimide; theobromine; thymine; triazine; tricyclododecane; uracil; xanthine; or derivatives thereof.

Preferred ring cores include substituted or unsubstituted glutarimide, methylthymine, methyluracil, thymine, theobromine, uracil and xanthine. Exemplary preferred cores include, but are not limited to: 1,3-cyclohexanedione, 1,3-cyclopentanedione; 1,3-dihydroxynaphthalene; 1-methyllumazine; methylbarbituric acid; 3,3- dimethylflutarimide; 2-hydroxypyridine; methyldihydroxypyrazolopyrimidine (preferably, 1,3-dimethyldihydroxypyrazolo[4,3-d]pyrimidine); methylpyrrolopyrimidine (preferably, 1-methylpyrrolo [2,3-d]pyrimidine); 2-pyrrole amides; 3-pyrrole amides; 1,2,3,4-tetrahydroisoquinolone; 1-methyl-2,4(1H,3H)-quinazolinedione (1-methylbenzoyleneurea); quinazolin-4(3H)-one; alkyl-substituted ($C_{1-6}$) thymine; methylthymine; alkyl-substituted ($C_{1-6}$) uracil; 6-aminouracil; 1-methyl-5,6-dihydrouracil; 1-methyluracil; 5- and/or 6-position substituted uracils; 1,7-dimethylxanthine, 3,7-dimethylxanthine; 3-methylxanthine; 3-methyl-7-methylpivaloylxanthine; 8-amino-3-methylxanthine; and 7-methylhypoxanthine.

Preferably, the ring-core is xanthine or a xanthine derivative. Especially preferred xanthine compounds have the following formula II:

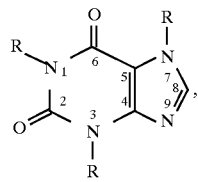

wherein R is selected from the foregoing members. Preferably, R is bonded to the $N_1$ xanthine nitrogen in formula I above and R, bonded to $N_3$ and $N_7$ xanthine nitrogens, are independently selected from the group consisting of hydrogen, methyl, fluoro, chloro and amino.

The invention provides a pharmaceutical composition comprising an inventive compound and a pharmaceutically acceptable excipient. The pharmaceutical composition may be formulated for oral, parenteral, ocular or topical administration to a patient.

The invention includes a method for treating an individual having a variety of diseases. The disease is characterized by or can be treated by inhibiting an immune response or a cellular response to external or in situ primary stimuli, the cellular response being mediated through a specific phospholipid-based second messenger acting adjacent to a cell membrane inner leaflet. The second messenger pathway is activated in response to various noxious or proliferative stimuli characteristic of a variety of disease states. More specifically, the invention includes methods for treating or preventing clinical symptoms of various disease states or reducing toxicity of other treatments by inhibiting cellular signaling through a second messenger pathway involving signaling through a non-arachidonyl phosphatidic acid intermediate.

A disease state or treatment-induced toxicity are selected from the group consisting of: tumor progression involving tumor stimulation of blood supply (angiogenesis) by production of fibroblast growth factor (FGF), vascular endothelial growth factor (VEGF) or platelet-derived growth factor (PDGF); tumor invasion and formation of metastases through adhesion molecule binding, expressed by vascular endothelial cells (VCAM and ICAM); tissue invasion through tumor metalloprotease production such as MMP-9; autoimmune diseases caused by dysregulation of the T cell or B cell immune systems, treatable by suppression of the T cell or B cell responses; acute allergic reactions including, but not limited to, asthma and chronic inflammatory diseases, mediated by pro-inflammatory cytokines including tumor necrosis factor (TNF) and IL-1, and rheumatoid arthritis, osteoarthritis, multiple sclerosis or insulin dependent diabetes mellitus (IDDM), associated with enhanced localization of inflammatory cells and release of inflammatory cytokines and metalloproteases; smooth muscle cell, endothelial cell, fibroblast and other cell type proliferation in response to growth factors, such as PDGF-AA, BB, FGF, EGF, etc. (i.e., atherosclerosis, restenosis, stroke, and coronary artery disease); activation of human immunodeficiency virus infection (AIDS and AIDS related complex); HIV-associated dementia; kidney mesengial cell proliferation in response to IL-1, MIP-1α, PDGF or FGF; inflammation; kidney glomerular or tubular toxicity in response to cyclosporin A or amphotericin B treatment; organ toxicity (e.g., gastrointestinal or pulmonary epithelial) in response to a cytotoxic therapy (e.g., cytotoxic drug or radiation); effects of non-alkylating anti-tumor agents; inflammation in response to inflammatory stimuli (e.g., TNF, L-1 and the like) characterized by production of metalloproteases or allergies due to degranulation of mast cells and basophils in response to IgE or RANTES; bone diseases caused by overproduction of osteoclast-activating factor (OAF) by osteoclasts; CNS diseases resulting from over-stimulation by proinflammatory neurotransmitters such as, acetylcholine, serotonin, leuenkephalin or glutamate; acute inflammatory diseases such as septic shock, adult respiratory distress syndrome; multi-organ dysfunction associated with inflammatory cytokine cascade; and combinations thereof.

In many cell types, signaling is dependent upon generation of a broad variety of non-arachidonyl PA species, some of which are generated from lyso-PA by the enzyme lyso-PA acyl transferase (LPAAT). Generation of each of these PA species (the predominant forms being: 1-acyl and 1-alkyl 2-linoleoyl PA compounds, generated by LPAAT) serves to effect both proliferative and/or inflammatory signaling in the diseases discussed and cell systems described above.

The inventive compounds are of particular significance for inhibiting IL-2-induced proliferative response. IL-2 signaling inhibition is potentially useful in the treatment of numerous disease states involving T-cell activation and hyperproliferation. Exemplary autoimmune diseases are lupus, scleroderma, rheumatoid arthritis, multiple sclerosis, glomerula nephritis, insulin dependent diabetes mellitas (IDDM), as well as potential malignancies, including but not limited to, chronic myelogenous leukemia as well as others.

BRIEF DESCRIPTION OF THE DRAWINGS

FIGS. 2A and 2B shows a comparison of CT1558 and cyclosporin A (CyA) for reversibility in the mixed lymphocyte reaction (MLR) demonstrating an ability of each compound to inhibit proliferative response to a stimulus when CT1558 or CyA was in contact with the cell and allow a proliferative response to resume when the drug is removed. The data presented in FIGS. 2A and 2B show that both CT1558 and CyA decreased proliferative response of mixed lymphocyte cells. However, after greater than 24 hours of treatment, CyA inhibition was irreversible whereas CT1558 inhibition was reversible.

DETAILED DESCRIPTION OF THE INVENTION

Figure 1:
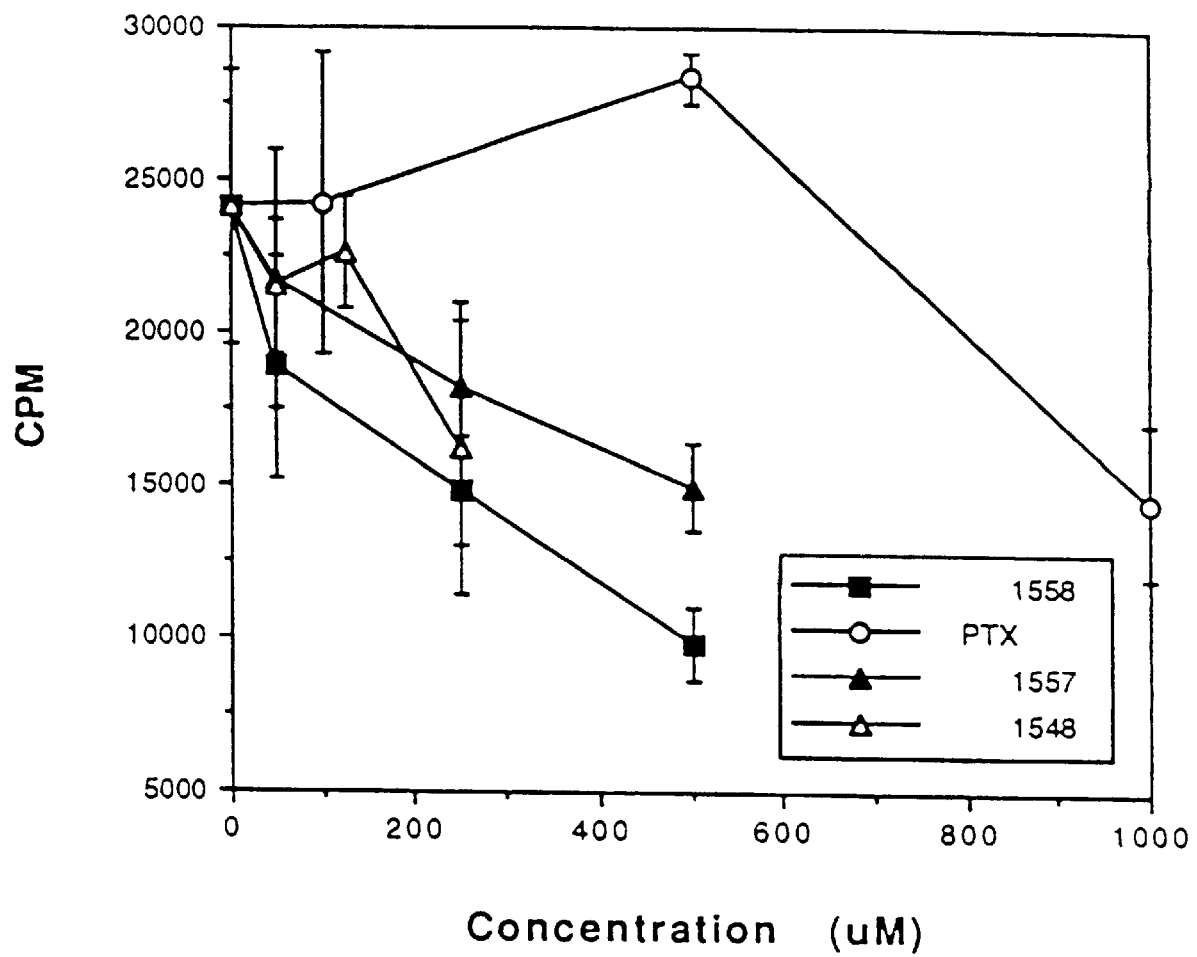
FIG. 1 shows a mixed lymphocyte reaction of PTX and three inventive compounds CT1558 (racemic N-(5-dimethylaminohexyl) 3,7-dimethylxanthine), CT1557 (racemic N-(5-methylaminohexyl) 3,7-dimethylxanthine), and CT1548 (racemic N-(7-aminooctyl) 3,7-dimethylxanthine). The mixed lymphocyte reaction shows a proliferative response of PBMC (peripheral blood mononuclear cells) to allogeneic stimulation determined in a two-way mixed lymphocyte reaction. Each of the inventive compounds tested was more effective than PTX in this immune modulating activity assay procedure.

The invention provides a genus of compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine

LPE=lysophosphoethanolamine

PA=phosphatidic acid

LPA=lysophosphatidic acid

DAG=diacylglycerol

LPLD=lysophospholipase-D

LPAAT=lysophosphatidic acid acyl transferase

PAPH=phosphatidic acid phosphohydrolase

PLA2=phospholipase A-2.

PLD=phospholipase D

PAA=phosphoarachidonic acid

PLA-2=phospholipase A2

PC=phosphatidyl choline

"remodeled" PA, cyclic pathway=PAA, LPA, PA and DAG intermediates substituted with 1-saturated, 2-linoleoyl or 1,2-dioleoyl, dioleoyl/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaenoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. Administration of the compounds of the invention reverse this elevation.

The compounds and pharmaceutical compositions of the invention include inhibitors of subspecies of LPAAT and PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI but rather derives from a PA that is largely composed of 1,2-diunsaturated and 1-alkyl, 2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

Each membrane phospholipid subclass (e.g., PA, PI, PE, PC and PS) reaches a stable content of characteristic fatty acyl side chains due to cyclic remodeling of the plasma membrane as well as turnover for each subclass. PA is often stable, but present in relatively small quantities. PA in resting cells consists mostly of saturated acyl chains, usually consisting of myristate, stearate and palmitate. In resting cells, PC's acyl side chains consist mostly of acyl palmitate in the sn-1 position and oleate in the sn-2 position. PE and PI are predominantly composed of sn-1 stearate and sn-2 arachidonate.

Due to this characteristic content of acyl groups in the sn-1 and sn-2 positions, the origin of any PA species may be deduced from the chemical nature of its acyl groups in the sn-1 and sn-2 positions. For example, if PA is derived from PC through action of the enzyme PLD, the PA will contain the characteristic acyl side chains of PC substrate passed through the second messenger pathway. Further, the origin of any 1,2 sn-substrate species may be differentiated as to its origin. However, it is important to know whether or not each phospholipid species passes through a PA form previous to hydrolysis to DAG. The lyso-PA that is converted to PA and thence to DAG may be shown. The complexities of this second messenger pathway can be sorted by suitable analyses by fatty acyl side chain chemistry (i.e., by thin layer chromatography, gas-liquid chromatography, or high pressure liquid chromatography) of intermediates in cells at various time points after stimulation of the second messenger pathway.

In certain meseachymal cells, such as neutrophils and rat or human mesangial cells, several signaling pathways may be activated in tandem, simultaneously or both. For example, in neutrophils, F-Met-Leu-Phe stimulates formation of PA through the action of PLD, followed in time by formation of DAG through the action of PAPH. Several minutes later, DAG is generated from PI through the classical phosphoinositide pathway. In many cells, DAG is derived from both PA that is being remodeled through a cycle whereby PA is sn-2 hydrolyzed by PLA-2, followed by sn-2 transacylation by LPAAT, and a PLD-pathway from PA that is generated from either PE or PC or both substrates by PLD.

The present second messenger pathway involves substrates with unsaturated fatty acids in the sn-2 position other than arachidonate and those sub species of PAPH and LPAAT that are not involved in normal cellular housekeeping functions that are part of the classical PI pathway. The PAPH and LPAAT enzymes involved in the present second messenger pathway are exquisitely stereo specific for different acyl side chains and isomeric forms of substrates. Therefore, the inventive compounds are preferably, substantially enantiomerically pure, and preferably are the R enantiomer at the chiral carbon atom bonded to the hydroxyl group.

PTX (in vitro) blocks formation of remodeled PA through the PA/DAG pathway at high PTX concentrations (greater than those that could be achieved in patients without dose-limiting side effects) by blocking formation of PA subspecies at LPAAT. Even in the presence of PTX, cells continue to form PA through the action of PLD, and DAG is also formed through the action of phospholipase C on PC and PI. The latter pathway are not inhibited by the inventive compounds or PTX. In PTX-treated cells, DAG derived from remodeled and PLA-generated PA is diminished (e.g., 1,2-sn-dioleoyl DAG, 1-alkyl, 2-linoleoyl DAG and 1-alkyl, 2-docosahexaneolyl DAG). Therefore, the inventive compounds and PTX inhibit the formation of only a certain species of PA and DAG by selectively inhibiting a specific second messenger pathway that is only activated in cells by noxious stimuli, but is not used to signal normal cellular housekeeping functions.

Therapeutic Uses of the Inventive Compounds

The specific activation inhibition of the second messenger pathway, as described above and activated primarily by various noxious stimuli, suggests that the inventive compounds are useful in treating a wide variety of clinical indications. Moreover, in vitro and in vivo data, presented herein, provides predictive data that a wide variety of clinical indications, having similar effects on the specific second messenger pathway, may be treated by the inventive compounds, which specifically inhibit the pathway, activated by noxious stimuli and mediated through, for example, inflammatory cytokines. In fact, the mechanism of action for the inventive compounds explains why these compounds have a multifarious clinical indications.

Activation of the second messenger pathway is a major mediator of response to noxious stimuli and results in cellular signals that lead to, for example, acute and chronic inflammation, immune response and cancer cell growth. However, all inhibitors do not inhibit all enzymes of this second messenger pathway. Although the inventive compounds may desirably inhibit many other unmentioned, noxious stimuli, they most effectively mediate the above conditions. Signals mediated by the present second messenger pathway include, for example, those cellular responses of LPS directly, T cell activation by antigen, B cell activation by antigen, cellular responses to IL-1 mediated through the IL-1 Type 1 receptor (but not the IL-1 Type 2 receptor), the TNF Type 1 receptor, growth stimulated by transformations including, but not limited to, activated oncogenes (e.g., ras, abl, her 2-neu and the like), smooth muscle cell proliferation stimulated by PDGF, b-FGF and IL-1; T cell and B cell growth stimulation by IL-2, IL-4 or IL-7 and IL-4 or IL-6, respectively; and more generally, T cell receptor signaling.

In vitro, the inventive compounds: (1) block IL-1 signal transduction through the Type 1 receptor as shown, for example, by preventing IL-1 and IL-1 plus PDGF (platelet derived growth factor) induction of proliferation of smooth muscle, endothelial and kidney mesengial cells; (2) suppress up regulation of adhesion molecules as shown, for example, by blocking VCAM in endothelial cells; (3) inhibit TNF, LPS and IL-1 induced metalloproteases (an inflammation model); (4) block LPS, TNF or IL-1 induced metalloprotease and secondary cytokine production (for prevention and treatment of septic shock); (5) suppress T cell and B cell activation by antigen, for example, IL-2 and IL-4; (6) inhibit mast cell activation by IgE; (7) are cytotoxic for transformed cells and tumor cell lines, yet not for normal cells; and (8) block signaling by IL-2, IL-4, IL-6 and IL-7 on T and B cells.

The foregoing in vitro effects give rise to the following in vivo biologic effects, including, but not limited to, protection and treatment of endotoxic shock and sepsis induced by gram positive or gram negative bacteria, inhibition of tumor cell growth, synergistic immunosuppression, active in autoimmune diseases and in suppressing allograft reactions, and stimulation of hair grow through reversal of an apoptotic process. The inventive compounds are most potent when used to prevent and treat septic shock, treat acute and chronic inflammatory disease, treat or prevent an autoimmune disease and stimulate hair growth (when applied topically).

The inventive compounds also are useful as an adjuvant to inhibit toxic side effects of drugs whose side effects are mediated through the present second messenger pathway.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus bFGF, a 72 kD type IV collagenase that is usually constitutive and induced by TNF or IL-1, and a stromelysin/PUMP-1 induced by TNF and IL-1. The inventive compounds can inhibit TNF or IL-1 induction of the 92 kD type V gelatinase inducable metalloprotease. Moreover, the inventive compounds can reduce PUMP-1 activity induced by 100 U/ml of IL-1. Accordingly, the inventive compounds prevent induction of certain metalloproteases induced by IL-1 or TNF and are not involved with constitutively produced proteases (e.g., 72 kD type IV collagenase) involved in normal tissue remodeling.

The inventive compounds inhibit signal transduction mediated through the Type I IL-1 receptor, and are therefore considered as IL-1 antagonists. A recent review article entitled "The Role of Interleukin-1 in Disease" (Dinarello and Wolff N. Engl. J. Med. 328, 106, Jan. 14, 1993) described the role of IL-1 as "an important rapid and direct determinant of disease." "In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." The article describes a group of diseases that are mediated by IL-1, including sepsis syndrome, rheumatoid arthritis, inflammatory bowel disease, acute and myelogenous leukemia, insulin-dependent diabetes mellitus, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds inhibit cellular signaling through the IL-1 Type I receptor and are IL-1 antagonists, the inventive compounds are useful for treating all of the above-mentioned diseases.

For example, for sepsis syndrome, the mechanism of IL-1-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of IL-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of IL-1 also rapidly decreases blood pressure, and doses of 300 ng or more per kilogram of body weight may cause severe hypotension. The therapeutic advantage of blocking the action of IL-1 resides in preventing its deleterious biologic effects without interfering with the production of molecules that have a role in homeostasis. The present inventive compounds address the need identified by Dinarello and Wolff by inhibiting cellular signaling only through the IL-1 Type I receptor and not through the IL-1 Type II receptor.

With regard to rheumatoid arthritis, Dinarello and Wolff state: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, interleukin-1 triggers the expression of genes for collagenases as well as phospholipases and cyclooxygenase, and blocking its action reduces bacterial-cell-wall-induced arthritis in rats." Therefore, the inventive compounds, as IL-1 antagonists, are useful to treat and prevent rheumatoid arthritis.

With regard to inflammatory bowel disease, ulcerative colitis and Crohn's disease are characterized by infiltrative lesions of the bowel that contain activated neutrophils and macrophages. IL-1 can stimulate production of inflammatory eicosanoids such as prostaglandin $E_2$ ($PGE_2$) and leukotriene $B_4$ ($LTB_4$) and IL-8, an inflammatory cytokine with neutrophil-chemoattractant and neutrophil-stimulating properties. Tissue concentrations of PGE2 and LTB4 correlate with the severity of disease in patients with ulcerative colitis, and tissue concentrations of IL-1 and IL-8 are high in patients with inflammatory bowel disease. Therefore, an IL-1 antagonist, such as the inventive compounds, would be effective to treat inflammatory bowel disease.

With regard to acute and chronic myelogenous leukemia, there is increasing evidence that IL-1 acts as a growth factor for such tumor cells. Therefore, the inventive compounds should be effective to prevent the growth of worsening of disease for acute and chronic myelogenous leukemias.

Insulin-dependent diabetes mellitus (IDDM) is considered to be an autoimmune disease with destruction of beta cells in the islets of Langerhans mediated by immunocompetent cells. Islets of animals with spontaneously occurring IDDM (e.g., BB rats or NOD mice) have inflammatory cells that contain IL-1. Therefore, the inventive compounds should be useful for the prevention of and treatment of IDDM.

IL-1 also plays a role in the development of atherosclerosis. Endothelial cells are a target of IL-1. IL-1 stimulates proliferation of vascular smooth muscle cells. Foam cells isolated from fatty arterial plaques from hypercholesterolemic rabbits contain IL-1β and IL-1β messenger RNA. The uptake of peripheral blood monocytes results in initiation of IL-1 production by these cells. IL-1 also stimulates production of PDGF. Taken together, IL-1 plays a part in the development of atherosclerotic lesions. Therefore, an IL-1 antagonist, such as the inventive compounds should be useful in preventing and treating atherosclerosis.

IL-1 activates (through the Type I IL-1 receptor) a lyso-PA acyltransferase (LPAAT) and phosphatidate phosphohydrolase within 5 seconds of cell (for example, human mesangial cells, HMC) exposure to this cytokine. Activation of both enzymes results in production of PA species with sn-1 and sn-2 unsaturated acyl groups, with the majority of sn-2 acyl chains being polyunsaturated. Both IL-1 and a product of LPAAT, 1,2-sn-dilinoleoyl PA, activate a signaling pathway involving hydrolysis of PE to PA. This reaction is followed by dephosphorylation of PA to produce both 1,2-sn-diacylglycerol, and 1-o-alkyl or 1-o-alkenyl acylglycerol (AAG) species. The inventive compounds exert their activity by inhibiting one or both enzymes at the inner leaflet of the plasma membrane. Therefore, appropriate in vitro models for drug activity is to measure inhibition of stimulation caused by a pro-inflammatory cytokine or other inflammatory cellular signal.

The generation of the sn-2 unsaturated PA fraction by LPAAT serves to activate either G-proteins, or acts directly upon PLD through alteration of its lipid microenvironment. Activation of LPAAT and generation of the sn-2-unsaturated PA species is an energy sensitive pathway of PLD. This provides a mechanism for a limited-receptor system to amplify a signal and generate a cellular response by rapid synthesis of small amounts of PA. Uptake of di-unsaturated PA, which is about <0.1% of total membrane lipid mass, is sufficient to activate PLD activity. This quantity of PA is similar to that endogeneously synthesized by LPAAT. The PA-stimulated PLD acts upon PE, which should be localized to the inner leaflet of the cell membrane, which is enriched in PE relative to the outer leaflet. Therefore, the cellular inflammatory response to IL-1 is mediated by the pathway: IL-1R→PA→(PLD)→PE. Whereas a localized tissue response is: lysoPA—PI→PKC→(PLD)→PC. The PLD species are likely to be different isozymes. The second messenger pathway whose activation is inhibited by the inventive compounds is not a PI-derived pathway and does not involve PKC in the time courses of inhibition. PKC is acutely activated by PI-derived DAG, but chronic activation (i.e., >30 min) is maintained by PC-derived PA generated by PC-directed PLD. Therefore, the pathway inhibited by the inventive compounds is PE-directed and not PC-directed. Moreover, the PE-directed PLD favors substrates with sn-2 long-chain unsaturation.

DAG and PA are upregulated in oncogenically transformed cells. For example, activating ras mutations result in increased generation of DAG on stimulation with mitogens, although the sources of DAG have differed between experimental systems. In nontransformed renal mesangial cells, IL-1β stimulation increased PLA2 and LPAAT activation, resulting in generation of sn-2 unsaturated PA and subsequent hydrolysis to DAG by phosphatidate phosphohydrolase. The ras transformation in NIH/3T3 cells upregulates serum-stimulated generation of DAG and PA. The specific species of DAG that is stimulated by serum is dioleoyl and for PA are dilinoleoyl and dioleoyl. This upregulation occurs over 4–12 hours and pretreatment of cells with an inventive compound, or PTX, blocks generation of these phospholipid second messengers. The inhibition occurs either through suppressing the generation of PA de novo from lysoPA, or through inhibition of one or both arms of the Lands cycle. The coordinate increase of lysoPA in the setting of diminished PA/DAG production suggests inhibition of transacylation of a precursor lipid. Therefore, the ras transformation mediates an upregulation of PA through indirect stimulation of PLA2 and/or LPAAT activity. The inventive compounds inhibit the conversion of the upregulated lysoPA to PA and subsequently block the phenotypic changes induced by PA/DAG in the membrane.

The ability of the inventive compounds to inhibit generation of unsaturated phospholipids is mirrored by the ability of inventive compounds to inhibit proliferation and tumorogenicity of ras-transformed cells in vitro and in vivo. PTX inhibits ras-transformed NIH/3T3 cells more than parental cells. This inhibition is reversible and is not associated with significant cytotoxicity.

Excessive or unregulated TNF (tumor necrosis factor) production is implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, AIDS or malignancy, AIDS, other viral infections (e.g., CMV, influenza, adenovirus, herpes family), keloid formation, scar tissue formation, Crohn's disease, ulcerative colitis, or pyresis. The inventive compounds or pharmaceutically acceptable salts thereof can be used in the manufacture of a medicament for the prophylactic or therapeutic treatment of any disease state in a human or other mammal, which is exacerbated or signaled through the present second messenger cellular phospholipid-based signaling pathway and by excessive or unregulated production of "first messenger" inflammatory cytokines such as TNF or IL-1. With regard to TNF first messenger signaling, there are several disease states in which excessive or unregulated TNF production by monocytes/macrophages is implicated in exacerbating or causing the disease. These include, for example, neurodegenerative diseases such as Alzheimers disease, endotoxemia or toxic shock syndrome (Tracey et al., *Nature* 330:662, 1987 and Hinshaw et al., *Circ. Shock* 30:279, 1990); cachexia (Dezube et al., *Lancet* 355:662, 1990), and adult respiratory distress syndrome (Miller et al., *Lancet* 2(8665):712, 1989). The inventive compounds may be used topically in the treatment of prophylaxis of topical disease states mediated or exacerbated by excessive TNF or IL-1, such as viral infections (herpes or viral conjunctivitis), psoriasis, fungal or yeast infections (ringworm, athletes foot, vaginitis, dandruff, etc.) or other dermatologic hyperproliferative disorders. High TNF levels have been implicated in acute malaria attacks (Grau et al., *N. Engl. J. Med.* 320:1585, 1989), chronic pulmonary inflammatory diseases such as silicosis and asbestosis (Piguet et al., *Nature* 344:245, 1990, and Bissonnette et al., *Inflammation* 13:329, 1989), and reperfusion injury (Vedder et al., *Proc. Natl. Acad. Sci. USA* 87:2643, 1990).

The inventive compounds provide a method for maintaining homeostasis in cells contacted by primary stimuli by mitigating the effects of these primary stimuli on the secondary signaling pathways invoked within seconds of a primary stimulus. For example, administration of an inventive compound in vivo or ex vivo provides a method to modify cellular behavior, the method comprising contacting cells (in vivo or ex vivo), whose behavior is to be modified, with an effective amount of an inventive compound or a pharmaceutical composition thereof wherein said method is a method to: (1) inhibit proliferation of tumor cells and said amount is sufficient to inhibit said proliferation; (2) suppress activation of T-cells by antigen or IL-2 stimulation, and said amount is sufficient to promote said activation; (3) suppress activation of monocyte/macrophage cells by endotoxin, TNF, IL-1 or GM-CSF stimulation and said amount is sufficient to suppress said activation; (4) suppress antibody production of B-cells in response to an antigen, IL-4 or CD40 ligand and said amount is sufficient to suppress said antibody production; (5) inhibit the proliferation of smooth muscle cells in response to growth factors capable of stimulating said proliferation and said amount is sufficient to inhibit said proliferation; (6) lower systemic vascular resistance conferred by endothelial cells and said amount is sufficient to reduce the release of hypertension-inducing substances; (7) lower systemic vascular resistance induced by endothelial cells and said amount is sufficient to enhance the release of anti-hypertensive substances; (8) lower expression of adhesion molecules induced by enhancers thereof, and said amount is sufficient to lower said expression; (9) suppress the activation of T-cells and macrophages by HIV and said amount is sufficient to suppress said activation thus inhibiting viral replication; (10) inhibit the proliferation of kidney mesangial cells in response to stimulation by IL-1 and/or MIP-1$\alpha$ and/or PDGF and/or FGF and said amount is sufficient to inhibit said proliferation; (11) enhance the resistance of kidney glomerular or tubular cells to cyclosporin A or amphotericin B and said amount is sufficient to enhance said resistance; (12) prevent the release of MIP-1$\alpha$ by IL-1, TNF, or endotoxin stimulated monocytes and macrophages; (13) prevent the release of platelet activating factor by IL-1, TNF, or endotoxin treated megakaryocytes, fibroblastic cells, and macrophages; (14) prevent the down-regulation of receptors for cytokines in TNF-treated hematopoietic progenitor cells and said amount is sufficient to prevent said down-regulation; (15) suppress the production of metalloproteases in IL-1-stimulated or TNF-stimulated glomerular epithelial cells or synovial cells and said amount is sufficient to enhance said production; (16) enhance the resistance of gastrointestinal or pulmonary epithelial cells to cytotoxic drugs or radiation and said amount is sufficient to enhance said resistance; (17) enhance the antitumor effect of a non-alkylating antitumor agent and said amount is sufficient to enhance said effect; (18) to inhibit the production of osteoclast activating factor in response to IL-1, and said amount is sufficient to inhibit said production; (19) inhibit degranulation in response to IgE, and said amount is sufficient to inhibit said degranulation; (20) enhance the release of adrenergic neural transmitters, dopamine, norepinephrine, or epinephrine, or the neurotransmitter, acetylcholine, and said amount is sufficient to enhance said release; (21) modulate the post-synaptic "slow current" effects of the adrenergic neurotransmitters dopamine, epinephrine, or norepinephrine, or the neurotransmitter acetylcholine, and said amount is sufficient to modulate such slow currents; (22) suppress signaling by neurotransmitters including acetyl choline, leuenkephalin and seretonin; or (23) increase seizure threshold.

The compounds of the invention can inhibit certain VEGF (vascular endothelial growth factor), FGF (fibroblast growth factor) and PDGF (platelet derived growth factor) effects in vivo, such as inhibition of angiogenesis or restenosis. For example, Ferns et al. (*Science* 253:1129, 1991) have shown that neointimal smooth muscle chemotaxis and angioplasty are inhibited in rats using a neutralizing antibody to PDGF. Also, Jawien et al. (*J. Clin Invest.* 89:507, 1992) have shown that PDGF promotes smooth muscle migration and intimal thickening in a rat model of balloon angioplasty. Inhibition of the PDGF-mediated effects following balloon angioplasty by the inventive compounds is the pharmacological rationale for using the inventive compounds as therapeutic agents to prevent restenosis. The inventive compounds also inhibit atherogenesis because increased levels of PDGF expressed by macrophages are associated with all phases of atherogenesis (Ross et al., *Science* 248:1009, 1990). Further, many human tumors express elevated levels of either PDGF, FGF, receptors for FGF or PDGF, or mutated cellular oncogenes highly homologous to these growth factors or their receptors. For example, such tumor cell lines include sarcoma cell lines (Leveen et al., *Int. J. Cancer* 46:1066, 1990), metastatic melanoma cells (Yamanishi et al., *Cancer Res.* 52:5024, 1992), and glial tumors (Fleming et al., *Cancer Res.* 52:4550, 1992).

Thus, the drugs of the invention are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

In Vitro Assays for Physiologic and Pharmacological Effects of the Inventive Compounds Various in vitro assays can be used to measure effects of the inventive compounds to module immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at 1000×g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 min at 37° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microtiter plate. Briefly, approximately $10^5$ test purified PBMC cells in 200 µl complete medium are co-cultured with approximately $10^5$ autologous (control culture) or allogeneic (stimulated culture) PBMC cells, wherein the allogeneic cells are from HLA disparate individuals. Varying doses of compounds (drug) are added at the time of addition of cells to the microtiter plate. The cultures are incubated for 6 days at 37° C. in a 5% $CO_2$ atmosphere. At the conclusion of the incubation tritiated thymidine is added (for example, 1 µCi/well of 40 to 60 Ci/mmole) and proliferation determined by liquid scintillation counting.

Another assay for measuring activity of the inventive compounds involves determining PDGF, FGF or VEGF proliferative response using either mouse NIH-3T3 (Balb) cells or human-derived stromal cells. Human stromal cells are plated (e.g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1α or TNF, and tritiated thymidine. Cell proliferation is determined by liquid scintillation counting.

A B-cell proliferation assay determines the effect of the inventive compounds on inhibiting proliferation of stimulated B-cells, stimulated by an anti-mu antibody (40 µg/ml), IL-4 or PMA (2.5 nM). Ramos B-cell tumor cells or murine splenocytes can be incubated with a stimulating agent, an inventive compound and tritiated thymidine to measure inhibition of cell proliferation caused by the stimulating agent.

Compounds of the Invention

We have found inventive compounds useful in a large variety of therapeutic indications for modulating disease by intracellular signaling through one or two specific intracellular signaling pathways. In addition, the inventive compounds and compositions are suitable for normal routes of therapeutic administration (e.g., parenteral, oral, ocular, topical, etc.) for providing effective dosages.

The invention provides a class of amine-derived compounds, preferably amine cyclic compounds. The inventive compounds and pharmaceutical compositions thereof have the formula:

(R)j- (core moiety), including resolved enantiomers and/or diastereomers, hydrates, salts, solvates and mixtures thereof, wherein j is an integer from one to three, the core moiety is either non-cyclic or comprises at least one five- to seven-membered ring structure, R may be selected from the group consisting of hydrogen, halogen (preferably bromine, chlorine, fluorine and iodine), hydroxyl, amino, substituted or unsubstituted benzyl, alkyl ($C_{1-6}$, preferably methyl) or alkenyl ($C_{1-6}$), preferably the alkyl or alkenyl groups being substituted by an hydroxy, halogen and dimethylamine and/or interrupted by an oxygen atom, wherein at least one R has the formula I:

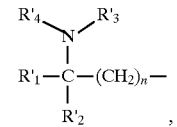

wherein n is an integer from four to eighteen; each $R'_1$ and $R'_2$ is independently hydrogen, alkyl ($C_{1-4}$) or alkenyl ($C_{1-4}$), the alkyl or alkenyl groups being preferably substituted by a halogen, hydroxyl, ketone or dimethylamino group and/or may be interrupted by an oxygen or hydrogen atom or an alkyl ($C_{1-4}$) group; and each $R'_3$ and $R'_4$ is independently hydrogen or methyl. Preferably, n is an integer from four to twelve (more preferably six to ten), $R'_1$ and $R'_2$ are independently hydrogen or methyl and $R'_3$ and $R'_4$ are hydrogen.

A non-cyclic core moiety may be, for example, an amino acid (one or two), an hydroxyl, carboxyl, sulfoxide, sulfonate, phosphate, amide, amine, or ketone group, a simple ionic functional group, or a terminal hydrogen or halogen atom. Exemplary core moiety amino acids may include one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be a dipeptide comprising two amino acids selected from the foregoing exemplary list. Exemplary core halogen atoms include bromine, chlorine, fluorine and iodine.

A core moiety may alternatively be at least one five- to seven-membered ring, preferably having from one to three, five- to six-membered ring structures in a predominantly planar configuration. Preferably, amino alkyl substituent R is bonded to a ring nitrogen if one exists. Exemplary, ring-core moieties may be substituted or unsubstituted: barbituric acid; benzamide; benzene; biphenyl; cyclohexane, cyclohexene; cyclohexanedione; cyclopentanedione; delta-lactam; flutarimide; glutarimide; homophthalimide; imidazole amide; isocarbostyrile; lumazine; napthlalene; pteridine; pthalimide; piperidine; pyridine; pyrimidine; pyrrole amide; quinazolinedione; quinazolinone; quinolone; recorsinol; stilbene; succinimide; theobromine; thymine; triazine; tricyclododecane; uracil; xanthine; or derivatives thereof.

Preferred ring cores include substituted or unsubstituted glutarimide, methylthymine, methyluracil, thymine, theobromine, uracil and xanthine. Exemplary preferred cores include, but are not limited to: 1,3-cyclohexanedione, 1,3-cyclopentanedione; 1,3-dihydroxynaphthalene; 1-methyllumazine; methylbarbituric acid; 3,3-dimethylflutarimide; 2 -hydroxypyridine; methyldihydroxypyrazolopyrimidine (preferably, 1,3-dimethyldihydroxypyrazolo[4,3-d]pyrimidine); methylpyrrolopyrimidine (preferably, 1-methylpyrrolo [2,3-d]pyrimidine); 2-pyrrole amides; 3-pyrrole amides; 1,2,3,4-tetrahydroisoquinolone; 1-methyl-2,4(1H,3H)-quinazolinedione (1-methylbenzoyleneurea); quinazolin-4 (3H)-one; alkyl-substituted ($C_{1-6}$) thymine; methylthymine; alkyl-substituted ($C_{1-6}$) uracil; 6-aminouracil; 1-methyl-5,6-dihydrouracil; 1-methyluracil; 5- and/or 6-position substituted uracils; 1,7-dimethylxanthine, 3,7-dimethylxanthine; 3-methylxanthine; 3-methyl-7-methylpivaloylxanthine; 8-amino-3-methylxanthine; and 7-methylhypoxanthine.

Preferably, the ring-core is xanthine or a xanthine derivative. Especially preferred xanthine compounds have the following formula II:

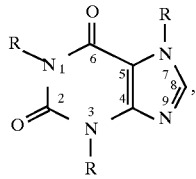

wherein R is selected from the foregoing members. Preferably, R is bonded to the $N_1$ xanthine nitrogen in formula I above and R, bonded to $N_3$ and $N_7$ xanthine nitrogens, are independently selected from the group consisting of hydrogen, methyl, fluoro, chloro and amino.

When j is two or three, remaining R substituents not having formula I may independently be hydrogen, halogen (preferably bromine, chlorine, fluorine and iodine), hydroxyl, amino, substituted or unsubstituted benzyl, alkyl ($C_{1-6}$, preferably methyl) or alkenyl ($C_{1-6}$), preferably the alkyl or alkenyl groups being substituted by an hydroxy, halogen and dimethylamine and/or interrupted by an oxygen atom. Preferred, exemplary R substituents not having formula I may include methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, and the like. Particularly preferred R substituents are ethyl, methyl, or hydrogen, most preferably, methyl and hydrogen. Particularly preferred compounds of the invention are exemplified herein.

The compounds of the invention may be provided as enantiomeric or diastereomeric mixtures or in resolved or partially resolved forms. Standard procedures are used for resolving optical isomers. Different enantiomeric variants (e.g., stereoisomers and chiral forms) of the inventive compound may have different drug activities, based upon their differential ability to inhibit PAPH and LPAAT. An optical isomer, substantially free of the corresponding enantiomer and/or diastereomers, is at least about 85% of a relevant optical isomer, preferably at least about 95% relevant optical isomer and especially at least about 99% or higher relevant optical isomer. Most preferably an amount of other optical forms is undetectable.

The invention provides a pharmaceutical composition comprising an inventive compound and a pharmaceutically acceptable excipient. The pharmaceutical composition may be formulated for oral, parenteral or topical administration to a patient.

The invention further provides a pharmaceutical composition comprising an inventive compound and a pharmaceutically acceptable excipient, the pharmaceutical composition being formulated for oral, parenteral or topical administration to a patient. A pharmaceutical composition may alternatively comprise one or a plurality of inventive compounds and a pharmaceutically acceptable carrier or excipient. Treatment of individuals with an inventive compound or pharmaceutical composition may include contacting with the inventive compound in vitro culture, in an extracorporeal treatment, or by administering (oral, parenteral or topical) the inventive compound or pharmaceutical composition to a subject whose cells are to be treated.

Exemplary, preferred compounds of the invention include both R and S enantiomers and racemic mixtures of the following compounds:

| | |
|---|---|
| CT1520 | 1-(5-Aminohexyl)-3,7-dimethylxanthine |
| CT1520.1 | dimer of CT1520 |
| CT1548 | 1-(7-Aminooctyl)-3,7-dimethylxanthine |
| CT1557 | 1-(5-Methylaminohexyl)-3,7-dimethylxanthine |
| CT1558 | 1-(5-Dimethylaminohexyl)-3,7-dimethylxanthine |
| CT3506 | 1-[5-(Undecylamino)hexyl]-3,7-dimethylxanthine |

The compounds of the invention further are able to decrease enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

While dosage values will vary, therapeutic efficacy is achieved when the compounds of the invention are administered to a human subject requiring such treatment as an effective oral, parenteral, or intravenous sublethal dose of about 50 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Coadministration With a P-450 Inhibitor

The coadministration in vivo of the compounds of the invention along with an inhibitor of P-450 results in an enhanced effect due to a longer half life of the inventive compounds. This in vivo effect is due to the inhibition of a degradation pathway for the compounds of the invention; in particular with respect to dealkylation at the N7 position of the xanthine core. For example, NIH3T3-D5C3 cells can be used to compare effects of a compound of Formula 1 alone or in combination with a P-450 inhibitor by comparing transformation phenotype among control, incubation with a compound of Formula 1 alone, and coincubation of a compound of Formula 1 with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60–100); cimetidine (400–2,400); ciprofloxacin (500–2000), enoxacin (500–2,000), norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); mexiletine (100–1,000); and dexamethasone (1–100 mg).

Pharmaceutical Formulations

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The inventive compounds and their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect on topical administration will, of course, vary with the compound chosen, the nature and severity of the disease and the discretion of the treatment provider.

Parenteral includes intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or non-aqueous carrier optionally containing a parenterally acceptable oil, for example polyethylene glycol, polyvinylpyrrolidone, lecithin, arachis oil, or sesame oil. The daily dosage for treatment of sepsis or another severe inflammatory condition via parenteral administration is suitable from about 0.001 mg/kg to about 40 mg/kg, preferably from about 0.01 mg/kg to about 20 mg/kg of an inventive compound or a pharmaceutically acceptable salt thereof calculated as the free base.

The inventive compounds may be administered orally. The daily dosage regimen for oral administration is suitably from about 0.1 mg/kg to about 1000 mg/kg per day. For administration the dosage is suitably form about 0.001 mg/kg to about 40 mg/kg of the inventive compound or a pharmaceutically acceptable salt thereof calculated as the free base. The active ingredient may be administered from 1 to 6 times a day, sufficient to exhibit activity.

The inventive compounds may be administered by inhalation (e.g., intranasal or oral) Appropriate dosage forms include an aerosol or a metered dose inhaler, as prepared by conventional techniques. The daily dosage is suitably form about 0.001 mg/kg to about 40 mg/kg of the inventive compound or a pharmaceutically acceptable salt thereof calculated as the free base. Typical compounds for inhalation are in the form of a solution, suspension or emulsion that may be administered as a dry powder or in the form of an aerosol using a conventional propellant.

The following examples, which should not be regarded as limiting in any way, illustrate the invention. In these examples PTX means Pentoxifylline.

EXAMPLE 1

This example illustrates a method for synthesis of 1-(5-aminohexyl)-3,7-dimethylxanthine. The method described in Koziara and Zwierzak, *Tetrahedron Letters* 28:6513–6516,1987 was followed to make CT1520. Briefly, boron trifluoride etherate (0.06 mol) was added dropwise at 10°–30° C. to a stirred solution of 1-(5-hydroxyhexyl)-3,7-dimethylxanthine (0.05 mol) and trimethylsilylazide (0.06 mol) in pentane (50 ml). After 24 hours at room temperature the mixture was poured into 100 mls of water. The organic phase was separated, washed with a 10% solution of sodium bicarbonate, and dried over sodium sulfate. The solution of the azide in pentane was stirred at 25°–30° C., and 0.05 mol of triethylphosphite was added. Stirring was continued for 6 hours, and the solution was left at this temperature for 72 hours. Solvent was evaporated off and the iminophosphorane was dissolved in ethanol (15 mls) and treated with p-toluenesulfonic acid monohydrate (0.05 mol) and water (0.05 mol). The mixture was refluxed for eight hours, evaporated and the residue diluted with 100 mls of ether. The tosyl salt of the amine was precipitated out and was recovered by filtration. Then, 30% aqueous ammonium hydroxide (20 mls) was added to the crystals and the free amine was extracted into dichloromethane (3×15 mls), dried over sodium sulfate and the solvent evaporated to yield the free amine as a viscous oil, 0.7 g with a 50% yield.

Another method to synthesize CT1520 begins with a solution of PTX (Sigma, 1.39 g, 5.0 mmol) in methanol (50 ml). Ammonium acetate (3.85 g, 50 mmol) was added and stirred for five minutes. Sodium cyanoborohydride (0.64 g, 10 mmol) was added to this solution, followed by 3 Å molecular sieves and this reaction mixture was stirred for 24 hours. The reaction mixture was filtered to remove solids. The solids were washed with dichloromethane (50 ml) and the filtrate was washed with water (50 ml). The aqueous phase was treated with saturated ammonium chloride solution (25 ml), stirred for 15 min and then a 30% aqueous ammonium hydroxide solution added (20 ml) to make the aqueous phase basic. The basic aqueous phase was extracted with 25% ethanol/dichloromethane (3×35 ml). The combined extracts were dried with magnesium sulfate. Solvent was evaporated under vacuum to provide a product as a viscous oil (0.95 g, 3.41 mmol, 68% yield).

EXAMPLE 2

This example illustrates a method for synthesis of 1-(7'-aminooctyl)-3,7-dimethylxanthine. 8-Bromo-2-octanone was used to alkylate the N1 position of theobromine as described in Example 1. The resulting 1-(2-octanone)-3,7-dimethylxanthine (5 mmol) was dissolved in 50 mls of methanol. Ammonium acetate (50 mmol) was added and the mixture was stirred for 5 minutes, vented to the outside. Sodium cyanoborohydride (10 mmol) was added, followed by 3 Å molecular sieves (3 scoops). After 24 hours of stirring, the mixture was filtered by gravity and the solids rinsed with 50 mls of dichloromethane. The combined filtrates were washed with 50 mls of water and dried with sodium sulfate, and the solvent was evaporated under vacuum. The residue was treated with 5% aqueous hydrochloride (25 mls) and then extracted with ether (2×20 mls). The aqueous layer was treated with saturated aqueous ammonium chloride solution (20 ml) and stirred for 15 minutes. Then, 30% aqueous ammonium hydroxide was added (30 mls) and the solution was extracted with 25% ethanol/dichloromethane (3×35 mls). The combined extracts were dried over magnesium sulfate and the solvents were evaporated under vacuum, providing 1.02 grams, 3.4 mmol, 68% yield of a viscous oil.

Another method to synthesize CT1548 begins with a suspension of NaH (580 mg, 24.2 mmol) in DMSO (100 ml) and added theobromine (3.96 g, 22.0 mmol). After 30 min, 8-bromo-1-octene (3.96 g, 22 mmol) was added and the reaction mixture was stirred for 16 hrs at 25° C. The reaction mixture was poured into 200 ml water and extracted with dichloromethane (3×50 ml). The organic portions were combined, washed with brine (50 ml), dried (sodium sulfate) and evaporated to provide 1-(7'-octenyl)-3,7-methylxanthine as a thick white oil which solidified upon standing (6.22 g, 97%). Two grams (6.89 mmol) of 1-(7'-octenyl)-3,7-methylxanthine was stirred in 5 ml water/6 ml sulfuric acid for 16 hrs. Water (100 ml) was added to the mixture and extracted with dichloromethane (3×50 ml). The organic portions were combined, dried (MgSO$_4$), and evaporated to give 1-(7'-hydroxyoctyl)-3,7-dimethylxanthine as an oil which solidified upon standing (1.80 g, 85% yield). 1-(7'-hydroxyoctyl)-3,7-dimethylxanthine (1.92 g, 6.22 mmol) in 10 ml dichloromethane was added to a solution of 2,2'-bipyridinium chlorochromate (2.73 g, 9.34 mM in dichloromethane (60 ml)). The reaction mixture was stirred for 16 hrs and Celite® (1 g) was added. The reaction mixture was filtered through a pad of celite, the filtrate was evaporated to a residue. The residue was re crystallized in dichloromethane/ether to give 1.52 g of the ketone (7'-oxooctyl)-3,7-dimethylxanthine as a slightly yellowish solid in an 80% yield. 7'-Oxooctyl-3,7-dimethylxanthine (192 mg, 0.63 mmol), ammonium acetate (438 mg, 6.3 mmol) and 4 Å molecular sieves (1 g) were stirred for 5 min, and NaBH$_3$CN (79 mg, 1.26 mmol) was added. This reaction mixture was stirred for 16 hrs and was then filtered to remove the sieves. The reaction was washed with Dichloromethane to remove any byproducts. The aqueous layer was treated with saturated aqueous NH$_4$Cl (25 ml) and concentrated NH$_4$OH (10 ml). The mixture was extracted with 25% ethanol/Dichloromethane (3×20 ml)). The organic portions were combined, dried (MgSO$_4$), and evaporated to give CT1548 (racemic mixture) as a purplish oil which slowly solidified upon standing (80 mg, 42% yield).

EXAMPLE 3

This example illustrates a method for Synthesis of 1-(10-aminoundecyl)-3,7-dimethylxanthine. 1-bromo-10-undecene is used in place of 8-bromo-2-octanone in the synthesis described in Examples 1 and 2 (first parts) for amino substituted xanthines. 1-bromo-10-undecene was converted to the ketone by a modification of the Wacker process, according to the method of Tsuji, *Synthesis* 369, 1984.

EXAMPLE 4

This example illustrates a synthesis method for CT1557 (N-(5-methylaminohexyl) 3,7-dimethylxanthine). A solution of PTX (2.0 g, 7.2 mmol) in methanol (50 ml) was added to methylamine hydrochloride (4.85 g, 72 mmol) and stirred for 5 min. Sodium cyanoborohydride (0.9 g, 14.4 mmol) was added and this solution was stirred for 48 hrs. This solution was treated with a saturated ammonium chloride solution (70 ml), stirred for 1 min, and then a 28% aqueous ammonium hydroxide solution (100 ml) was added. The solution was extracted with dichloromethane (3×50 ml) and the combined extracts were dried (magnesium sulfate). The solvent was evaporated to give the product as a viscous oil (2.08 g, 7.10 mmol, 98% yield).

EXAMPLE 5

This example illustrates a method to synthesize CT1558 (N-(5-dimethylaminohexyl) 3,7-dimethylxanthine). A solution of PTX (2.0 g, 7.2 mmol) in methanol (50 ml) was added to dimethylamine hydrochloride (5.86 g, 72 mmol) and stirred for 5 min. Sodium cyanoborohydride (0.9 g, 14.4 mmol) was added and this solution was stirred for 42 hrs. This solution was treated with a saturated ammonium chloride solution (70 ml), stirred for 1 min, and then a 28% aqueous ammonium hydroxide solution (50 ml) was added. The solution was extracted with dichloromethane (3×40 ml) and the combined extracts were washed with water (30 ml), and dried (magnesium sulfate). The solvent was evaporated under vacuum to give the product as a viscous oil (2.20 g, 7.10 mmol, 99% yield).

EXAMPLE 6

This example illustrates effects of CT1558, CT1557 and CT1548 on a proliferative response of PBMCs to allogeneic stimulation determined in a two-way mixed lymphocyte reaction. The two way mixed lymphocyte reaction procedure is described herein. Briefly, $10_5$ responder PBMC in 200 μl complete medium were co-cultured with $10_5$ allogeneic cells. Autologous control cultures produced counts less than 1000. Drug was added contemporaneous with cells. The cultures were incubated for 6 days and labeled with tritiated thymidine to measure cell proliferation. Each of the inventive compounds were more effective than PTX for modulating immune activity in this assay (FIG. 1).

EXAMPLE 7

Figure 2A:
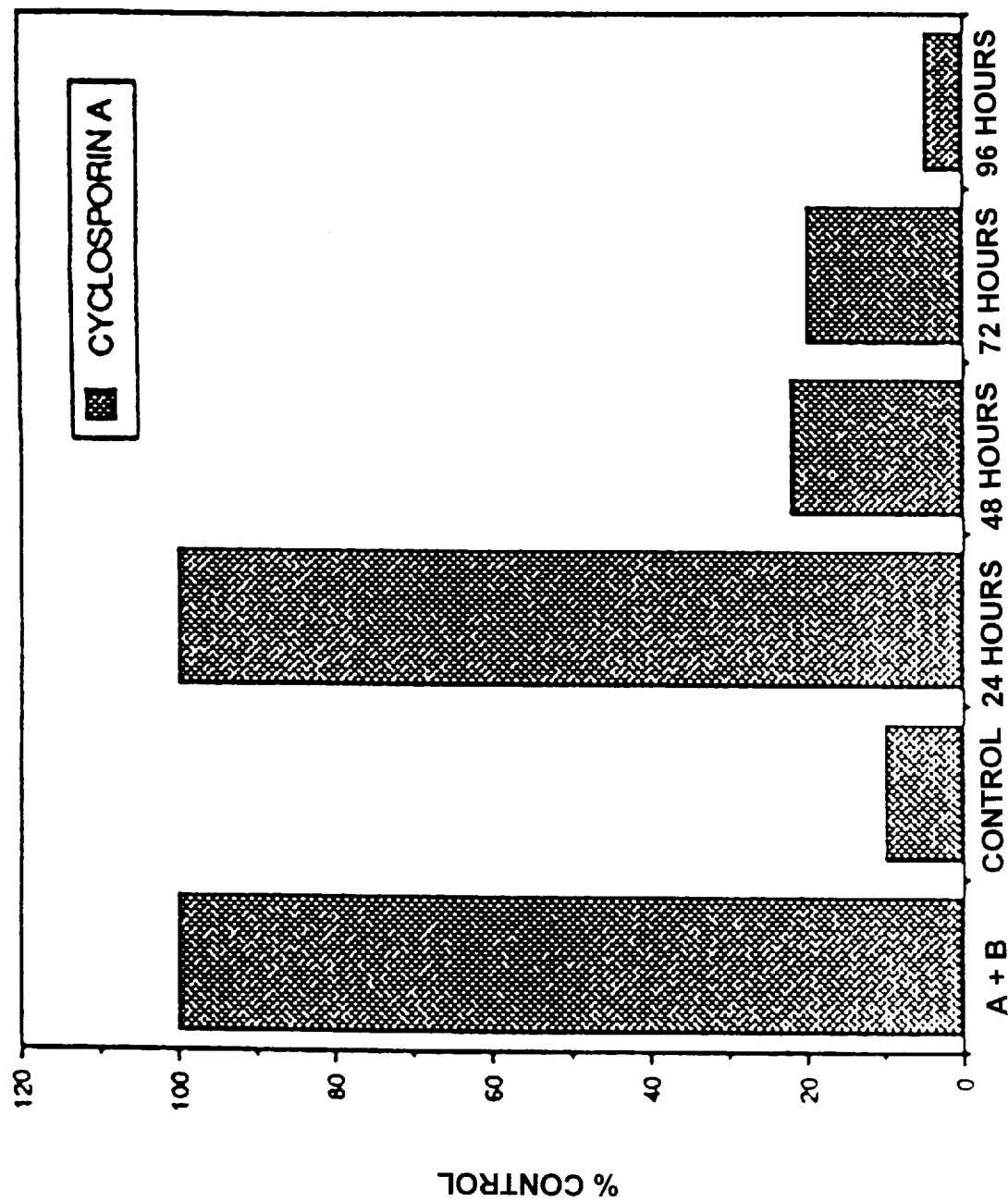

This example illustrates reversible effects of CT1558 and cyclosporin A (CyA) in a reversible mixed lymphocyte assay. This assay compares the ability of each drug to inhibit the proliferative response when the drug is in contact with cells and to allow the proliferative response to resume following drug removal. The culture were treated with 350 µg CT1558 or 3.3 µg/ml cyclosporin A continuously for 6 days prior to pulsing with tritiated thymidine. Alternatively, the cultures were treated with drug for 24, 48, 72, or 96 hrs prior to washing and resuspending in drug-free media and then pulsed with tritiated thymidine. The results in FIGS. 2A and 2B indicate that CT1558 and CyA decrease the proliferative response. However, CyA inhibition is irreversible whereas CT1558 inhibition is reversible.

EXAMPLE 8

Figure 3:
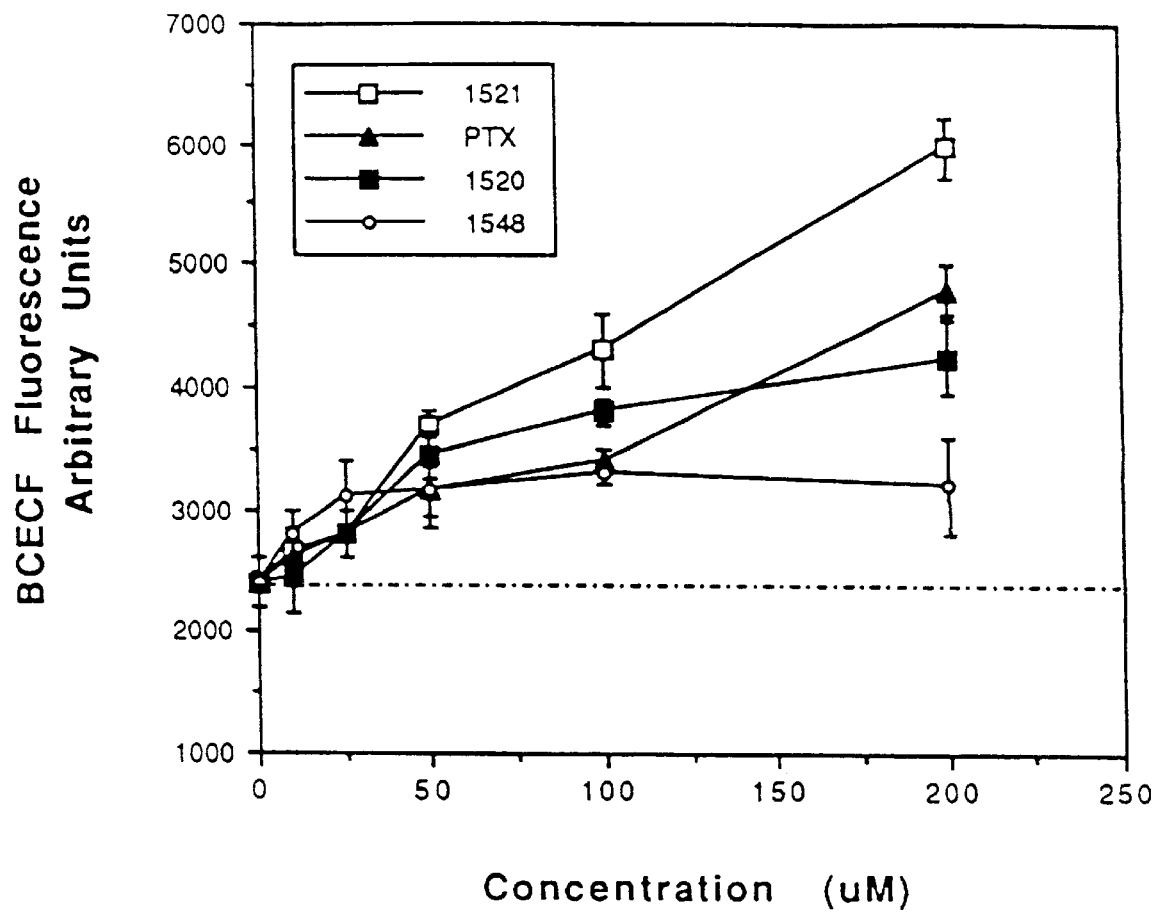
FIG. 3 shows an effect of CT1520 (racemate of N-(5-aminohexyl) 3,7-dimethylxanthine) and CT1548, for protection of L929 cells from treatment with a toxic level of TNF (tumor necrosis factor, 300 ng/ml). For comparison, the results with PTX and another compound are also shown. The most potent results were seen for CT 1520 and CT1548. This is an in vitro predictive model for treatment and prevention of septic shock.

This example illustrates the effects of CT 1520, CT 1548, CT 1521 and PTX for protection of mouse L929 cells from cytotoxic effects of TNF. This procedure is an in vitro septic shock model. L929 cells ($10^5$/well) were treated with 300 ng/ml of human TNF with or without drug (added one hour prior to TNF addition) at concentrations shown in FIG. 3. One day later the cells were stained for viability using BCECF and fluorescence analyzed for viability using a Milipore fluorescence plate reader. The results shown in FIG. 3 illustrate that the most potent cytoprotective effects were seen with CT1520 and CT1548.

EXAMPLE 9

Figure 4:
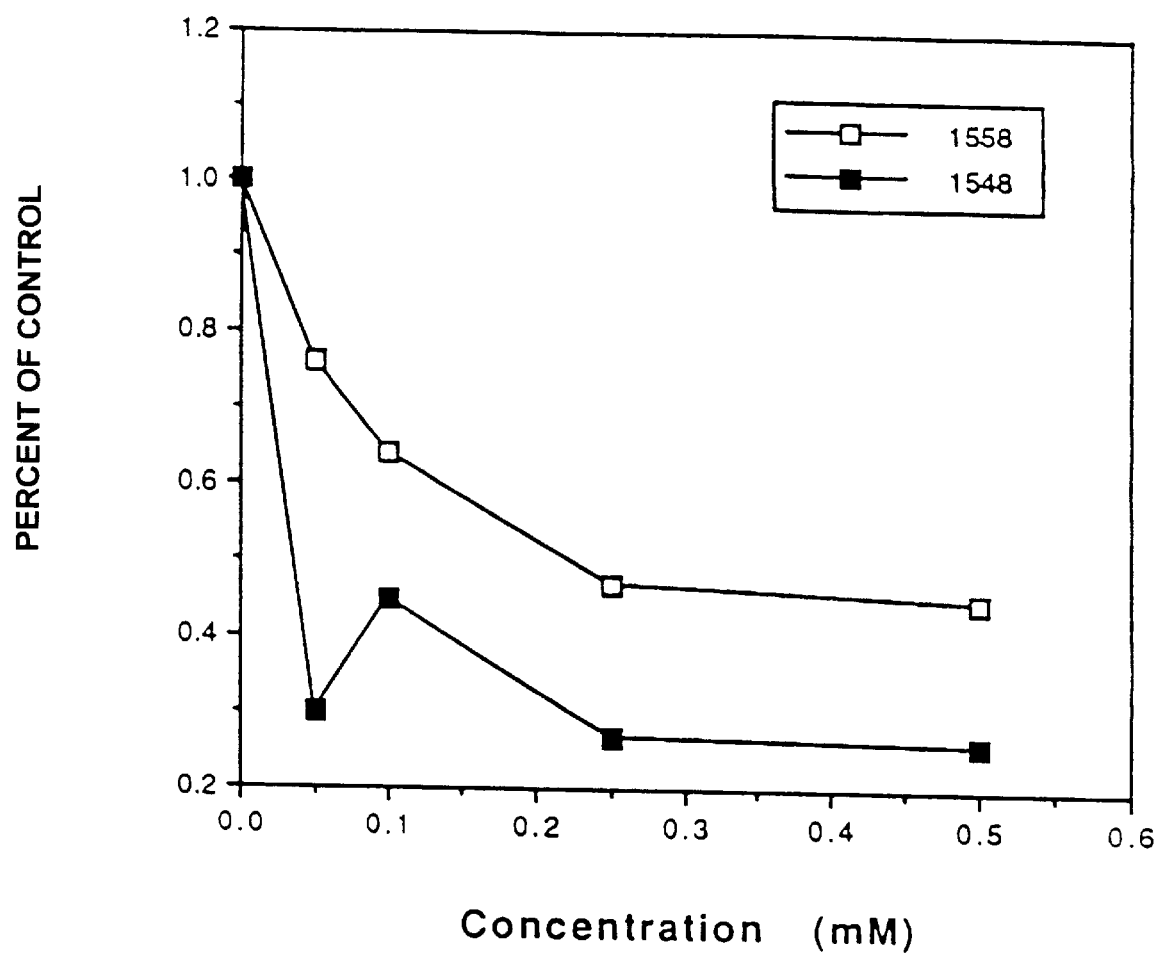
FIG. 4 shows the effects of CT1558 and CT1548 on PDGF-induced (platelet derived growth factor) proliferation in human stromal cells. Background counts were approximately 10% of control levels.

This example illustrates the effects of CT1548 and CT1558 on inhibition of PDGF-induced proliferation in human stromal cells. Human stromal cells were starved in serum-free media for 24 hours and then stimulated with 50 ng/ml PDGF-BB. The drugs were added at various concentrations one hour prior to PDGF stimulation. Tritiated thymidine was added at the time of PDGF stimulation and pulsed for 24 hours. Cells were harvested and cell proliferation measured (FIG. 4). Background counts (i.e., starved cells) were about 10% of control levels.

EXAMPLE 10

Figure 5:
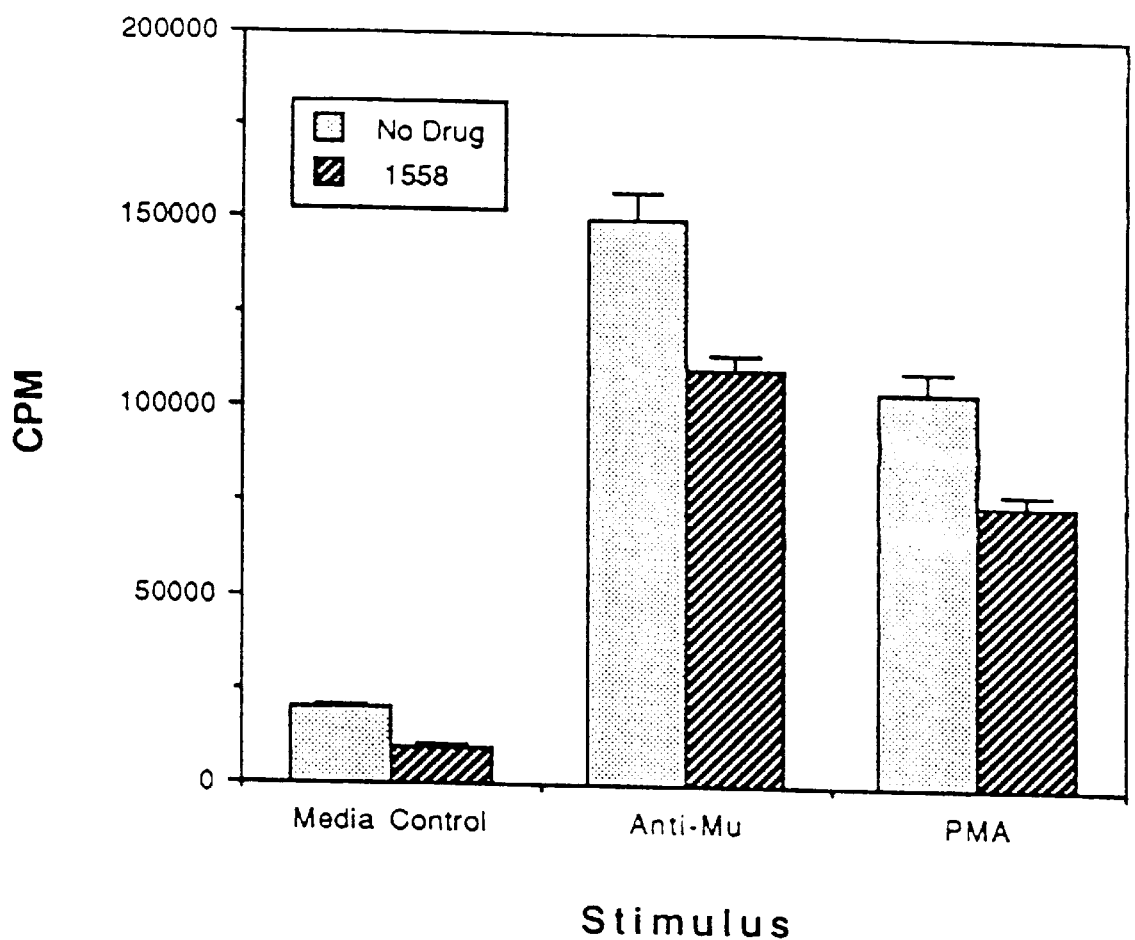
FIG. 5 shows the effect of CT1558 to inhibit proliferation of a Ramos B-cell tumor line after stimulation with either an anti-mu antibody or PMA (phorbol myristic acid). CT1558 inhibited some of the proliferative response to anti-mu and PMA.

This example illustrates the effects of CT1558 (250 µµoλ) to inhibit B cell proliferation. Ramos B-cell tumor cells were treated with CT1558 for one hr prior to stimulation with anti-mu antibody or PMA (5 nM). One day later the cells were pulsed with tritiated thymidine and proliferation determined (FIG. 5). CT1558 inhibited the proliferative response.

EXAMPLE 11

Figure 6:
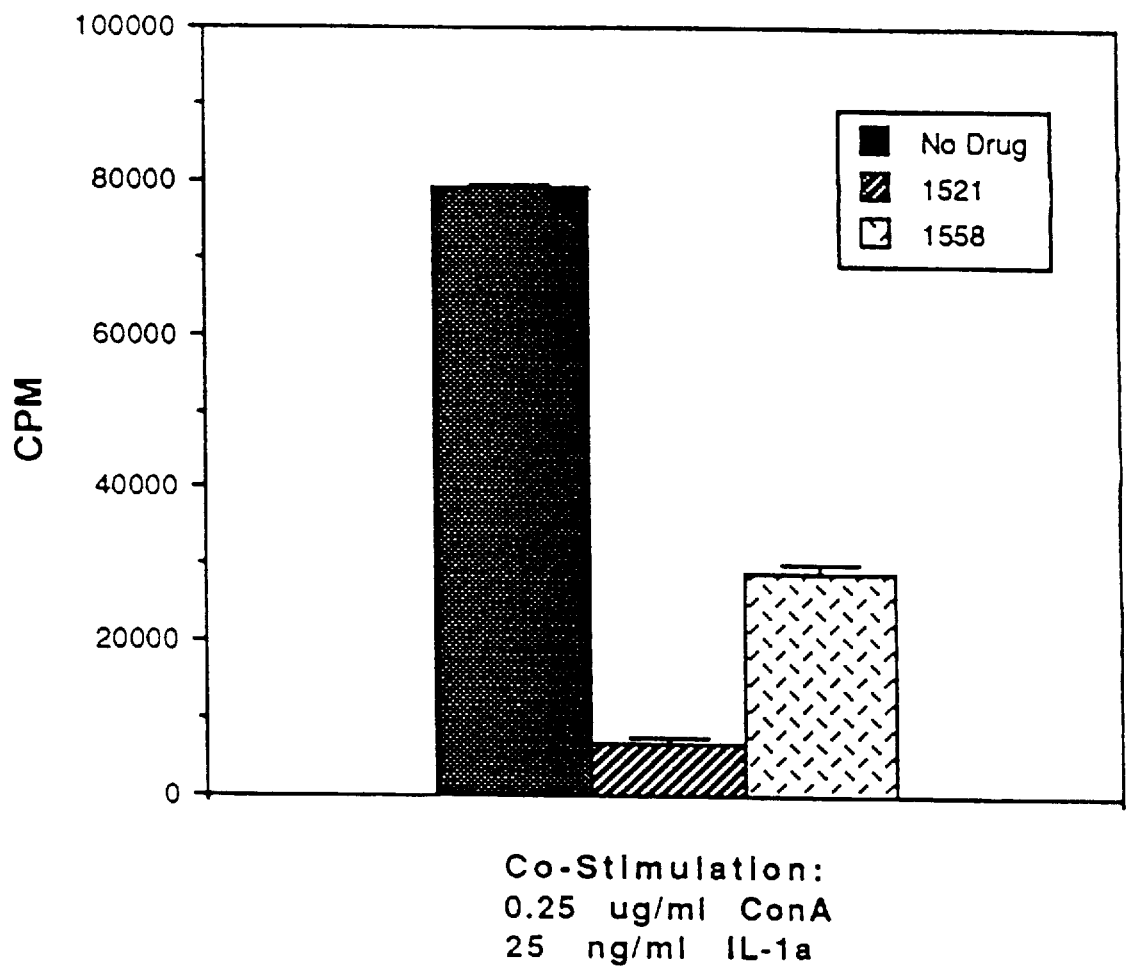
FIG. 6 shows a thymocyte proliferation assay wherein thymocyte proliferation is stimulated by Con A and IL-1α. Both CT1521 and CT1558 inhibited proliferation in thymocytes.

This example illustrates the effects of CT1521 and CT1558 on thymocyte proliferation stimulated by IL-1 or Con A. The data are shown in FIG. 6. Drugs were added 2 hrs prior to stimulation. Both drugs inhibited the proliferation of thymocytes.

EXAMPLE 12

This example illustrates a method to synthesize 1-(6-Hydroxyhexyl)-3,7-dimethylxanthine. A mixture of theobromine (1.0 g, 5.5 mmol, from Sigma) and 50% sodium hydride in oil (264 mg, 5.5 mmol) and dimethylsulfoxide (20 mL) was stirred for 50 minutes, after which 6-bromo-1-hexanol (1.0 g, 5.5 mmol, from Aldrich) was added. After stirring for 18 hours, the solution was treated with water (50 mL) and then extracted with two 25 mL aliquots of hexane. The aqueous phase was extracted with 25% ethanol-dichloromethane (3×35 mL) and the combined ethanol-dichloromethane extracts dried over magnesium sulfate. The solvents were evaporated under vacuum. The remaining dimethylsulfoxide was removed by distillation under full pump vacuum to yield 1.4 g 1-(6-hydroxyhexyl)-3,7-dimethylxanthine (91% yield) as a white powder.

Dimethyl sulfoxide (156 mL, 172 mg, 2.2 mmol) was slowly added to a solution of oxalyl chloride (103 mL, 150 mg, 1.2 mmol) at −78° C. A solution of 1-(6-hydroxyhexyl)-3,7-dimethylxanthine (300 mg, 1.1 mmol) in methylene chloride (5 mL) was added, followed by 15 minutes of stirring. The cold bath was removed after addition of triethylamine (765 mL, 555 mg, 5.5 mmol). The reaction was added at room temperature to 20 mL water and extracted with methylene chloride (3×50 mL). The organic layers were combined and washed with 1% hydrogen chloride (20 mL), saturated sodium bicarbonate (20 mL), and brine (20 mL) and then dried over sodium sulfate. Evaporation of solvent and recrystallization of the residue in chloroform/petroleum ether yields 267 mg 1-(6-oxohexyl)-3,7-dimethylxanthine (87% yield).

Sodium cyanoborohydride (63 mg, 1.0 mmol) was added to a mixture of 1-(6-oxohexyl)-3,7-dimethylxanthine (150 mg, 0.5 mmol), undecylamine (0.43 mL, 2.5 mmol), 38% aqueous hydrochloric acid solution (0.2 mL, 2.5 mmol), methanol (5 mL), and tetrahydrofuran (5 mL). The resulting mixture was stirred for 48 hours. Saturated aqueous ammonium chloride solution (20 mL) was added to the stirred mixture, followed by an additional 20 minutes of stirring and addition of 30% aqueous ammonium hydroxide solution (30 mL). The mixture was extracted with 25% methanol-dichloromethane (3×mL) and the combined extracts dried over sodium sulfate. The solvents were evaporated under vacuum, resulting in 190 mg of 1-[5-(Undecylamino)hexyl]-3,7-dimethylxanthine (86% yield).

EXAMPLE 13

Figure 7:
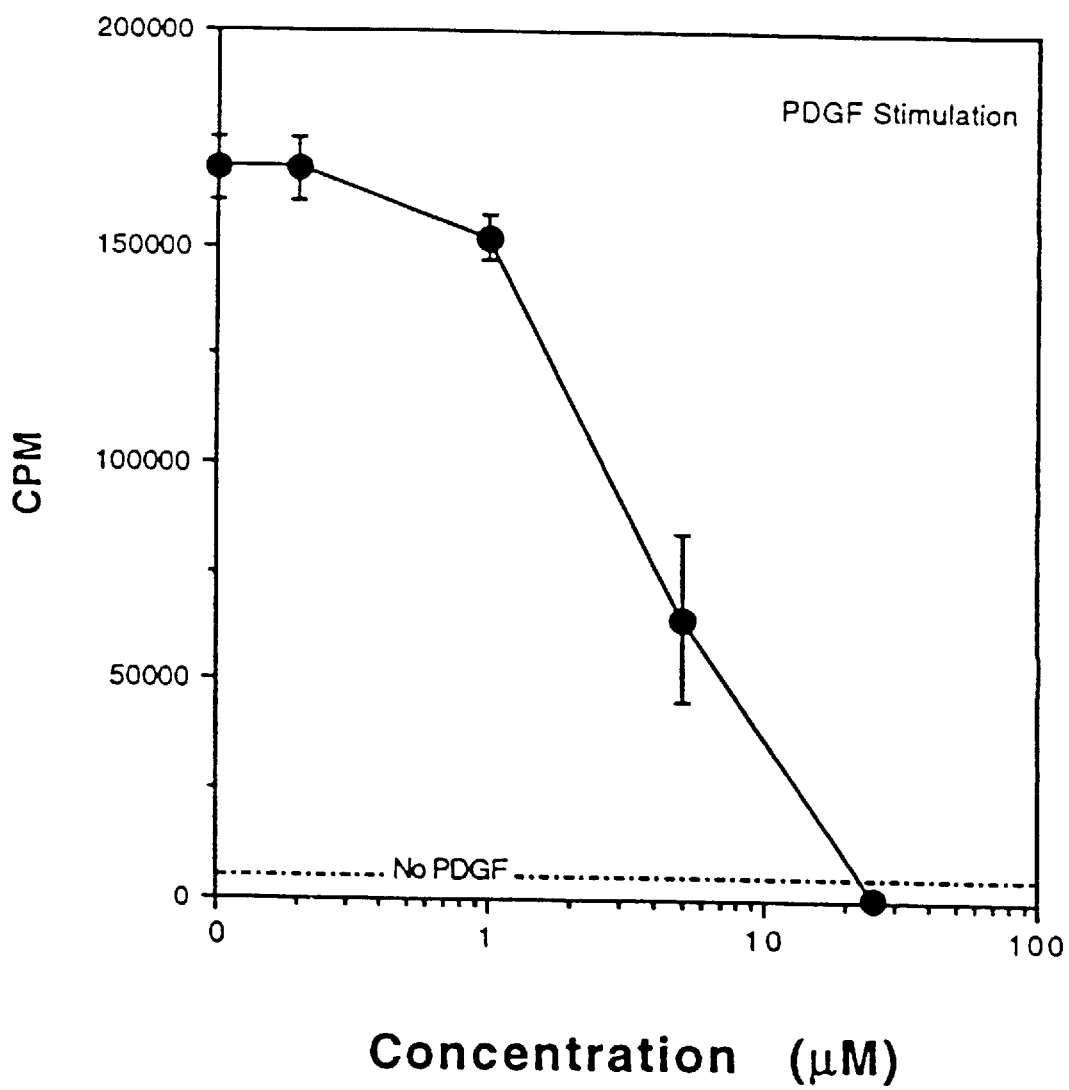
FIG. 7 shows the effects of 1-[5-(undecylamino)hexyl]-3,7-dimethylxanthine on PDGF-induced proliferation in human stromal cells.

This example shows the effects of 1-[5-(undecylamino) hexyl]-3,7-dimethylxanthine on PDGF-induced proliferation in human stromal cells. As in Example 9, human stromal cells were starved in serum-free media for 24 hours and then stimulated with 50 ng/ml PDGF-BB. The drugs were added at various concentrations one hour prior to PDGF stimulation. Tritiated thymidine was added at the time of PDGF stimulation and pulsed for 24 hours. Cells were harvested and cell proliferation measured having background counts (i.e., starved cells) at about 10% of control levels. FIG. 7 illustrates the inventive compound's inhibition of PDGF-induced proliferation at various concentrations (µM).

EXAMPLE 14

This example shows an inhibitive effect of the inventive compound 1-[5-(undecylamino)hexyl]-3,7-dimethylxanthine on thymocyte proliferation and activation at various concentrations of the compounds (IC50) for murine thymocyte proliferation co-stimulated by Concanavalin A (Con A) and interleukin-2 alpha (IL-2). Con A, used to activate CD3, along with IL-2 co-stimulation, induces T cell proliferation and differentiation.

Figure 8:
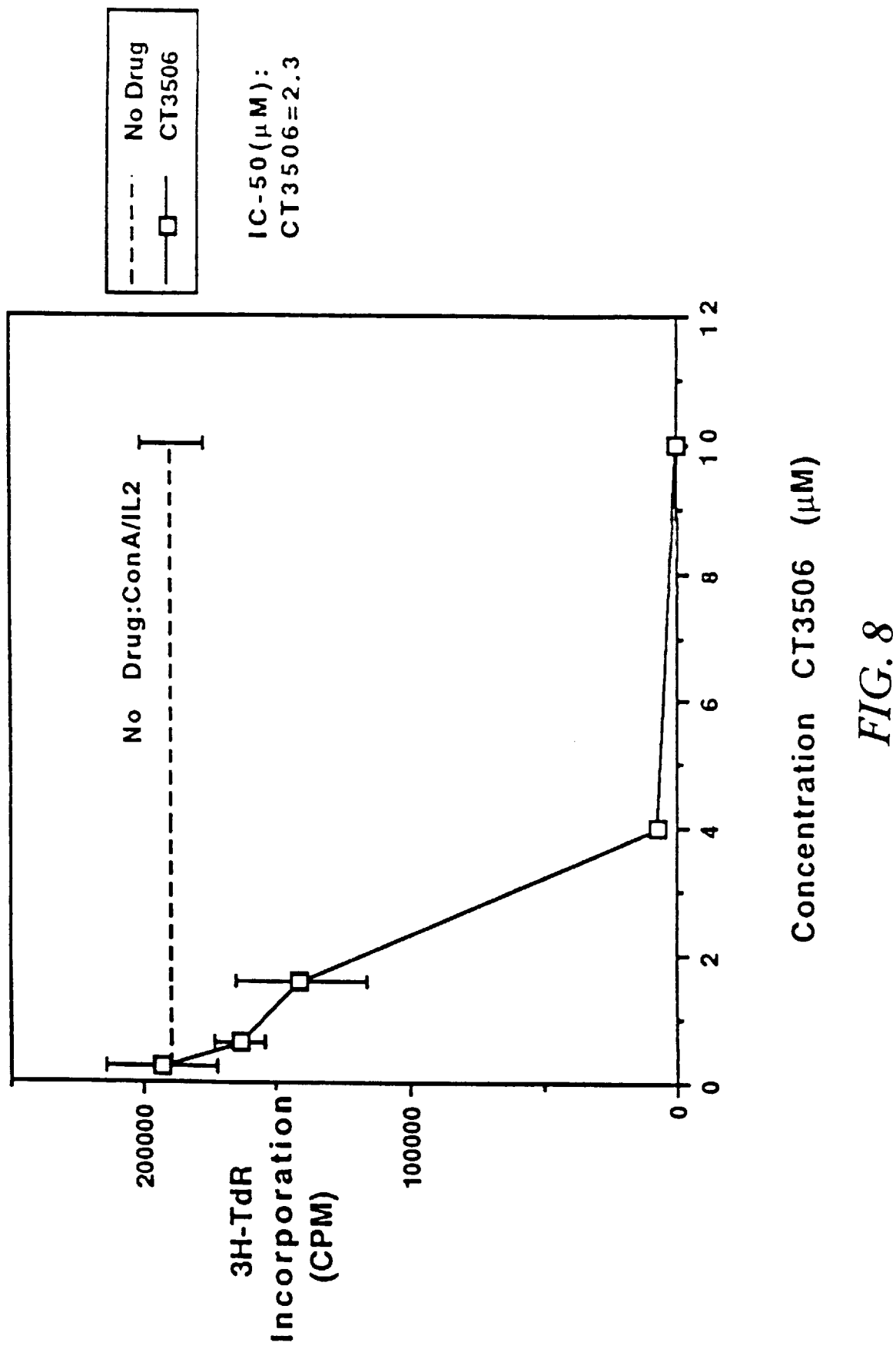
FIG. 8 shows inhibition effects on a mixed lymphocyte proliferation and activation, costimulated with Con A and IL-2 reaction of inventive compound 1-[5-(undecylamino) hexyl]-3,7-dimethylxanthine. The inventive compound tested inhibit thymocyte proliferation and activation at various concentrations of the compound.

Thymuses, obtained from normal, female Balb/C mice, were dissociated and plated into 96-well plates at a density of $2\times10^5$ cells/well. Con A (0.25 mg/ml) and IL-2 (15 U/ml) were added to the wells. The cells were incubated for 4 days at 37° C. On day 4, the cells were pulsed with tritiated thymidine and incubated for an additional 4 hours. Incorporated tritiated thymidine of harvested cells was determined in a liquid scintillation counter. Drug doses (shown in FIG. 8, μM) were added two hours prior to Con A and IL-2 activation. Background counts were less than 200 cpm. The inventive compounds tested inhibit thymocyte proliferation and activation at relatively low concentrations with an IC50 value of 2.3 μM.

What is claimed is:

1. A compound having the formula:

(R)j- (core moiety), having resolved enantiomers, diastereomers, hydrates, salts, and solvates thereof, wherein j is an integer from one to three, the core moiety is xanthinyl or xanthinyl derivative, R is selected from the group consisting of hydrogen, halogen, hydroxyl, amino, benzyl, alkyl ($C_{1-6}$) or alkenyl ($C_{1-6}$), and at least one R has the formula I:

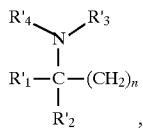

wherein n is an integer from four to eighteen; each $R'_1$ and $R'_2$ is independently selected from the group consisting of hydrogen, alkyl ($C_{1-4}$) or alkenyl ($C_{1-4}$); and each $R'_3$ and $R'_4$ is independently selected from the group consisting of hydrogen or methyl.

2. The compound of claim 1, wherein the $R'_1$ or $R'_2$ alkyl or alkenyl is interrupted by a member selected from the group consisting of oxygen, hydrogen atom and alkyl ($C_{1-4}$).

3. The compound of claim 1, wherein n is an integer from four to twelve.

4. The compound of claim 1, wherein $R'_1$ and $R'_2$ are independently hydrogen or methyl.

5. The compound of claim 1, wherein amino alkyl substituent R is bonded to a ring nitrogen.

6. A pharmaceutical composition comprising a compound of claim 1 in admixture with a pharmaceutically acceptable excipient or carrier.

7. The compound of claim 1, wherein the compound is selected from the group consisting of: 1-(5-aminohexyl)-3,7-dimethylxanthine; dimer of 1-(5-aminohexyl)-3,7-dimethylxanthine; 1-(7-aminooctyl)-3,7-dimethylxanthine; 1-(5-methylarninohexyl)-3,7-dimethylxanthine; and 1-(5-dimethylaminohexyl)-3,7-dimethylxanthine.

8. The compound of claim 1, wherein the core moiety is selected from the group consisting of 1,7-dimethylxanthinyl, 3,7-dimethylxanthinyl, 3-methylxanthinyl, 3-methyl-7-methylpivaloylxanthinyl, 8-amino-3-methylxanthinyl and 7-methylhypoxanthinyl.

9. The compound of claim 1, wherein the at least one R having formula I is attached to the $N_1$ position of the core moiety.

* * * * *

UNITED STATES PATENT AND TRADEMARK OFFICE
CERTIFICATE OF CORRECTION

PATENT NO. : 5,889,011
DATED : March 30, 1999
INVENTOR(S) : J. Peter KLEIN et al.

It is certified that error appears in the above-identified patent and that said Letters Patent is hereby corrected as shown below:

In the Claims:

Claim 1, line 20, change "$(CH_2)n$" to --$(CH_2)n$- --

Claim 7, line 17, change "methylarninohexyl" to --methylaminohexyl--

Signed and Sealed this

Twenty-first Day of September, 1999

*Attest:*

Q. TODD DICKINSON

*Attesting Officer*   Acting Commissioner of Patents and Trademarks